United States Patent [19]

Brenner et al.

[11] 3,940,430

[45] Feb. 24, 1976

[54] SILANIZED ANTIMICROBIAL COMPOUNDS

[75] Inventors: Mortimer Wilkes Brenner, Scarsdale; Louis Laufer, New York, both of N.Y.

[73] Assignee: Schwarz Services International Ltd., Mount Vernon, N.Y.

[22] Filed: Aug. 28, 1974

[21] Appl. No.: 501,058

[52] U.S. Cl............................ 260/448.8 R; 424/184
[51] Int. Cl.$^2$..... C07F 7/06; C07F 7/10; C07F 7/18
[58] Field of Search............................ 260/448.8 R

[56] References Cited
UNITED STATES PATENTS

| | | | |
|---|---|---|---|
| 3,423,445 | 1/1969 | Holbrook et al. | 260/448.8 R X |
| 3,489,783 | 1/1970 | Shepard et al. | 260/448.8 R |
| 3,546,267 | 12/1970 | Ismail et al. | 260/448.8 R |
| 3,636,026 | 1/1972 | Fuhr et al. | 260/448.8 R |
| 3,803,194 | 4/1974 | Golitz et al. | 260/448.8 R X |

*Primary Examiner*—Paul F. Shaver
*Attorney, Agent, or Firm*—St. Onge Mayers Steward & Reens

[57] ABSTRACT

Silanized antimicrobial compounds are disclosed which are the reaction products of chlorinated phenols, bis-phenols, dihydric phenols, hydroxy diphenyl ethers and ortho or para hydroxybenzoic acids and their lower alkyl esters with an amino substituted silane having the general formula $NH_2(CH_2)_n Si(R)_3$ wherein R is methoxy, ethoxy or propoxy and $n$ is 2, 3, or 4.

The silane moiety is joined to the antimicrobial compound through the oxygen of a hydroxyl group of the starting compound.

26 Claims, No Drawings

SILANIZED ANTIMICROBIAL COMPOUNDS

BACKGROUND OF THE INVENTION

This invention relates to silanized antimicrobial compounds and more particularly to silanized chlorinated phenols, bis-phenols, dihydric phenols, hydroxy diphenyl ethers, and ortho or para hydroxybenzoic acids and their lower alkyl esters. The compounds are the reaction product of an antimicrobial phenol or the like with an amino substituted silane of the general formula $$NH_2(CH_3Si(R)_3$$

wherein R is methoxy, ethoxy or propoxy, and $n$ is 2, 3, or 4.

In the preparing and packaging of substances such as pharmaceuticals, foods and beverages, microbial contamination is a major problem. In the packaging industry it is necessary to maintain containers and packaging apparatus in sterile or near sterile condition to prevent or minimize the inclusion or growth of undesirable microbes in the packaged pharmaceuticals, foods or beverages. In the preparation and serving of food, as in restaurants, hotels or other institutions, there is a problem of microbial contamination as the foods are handled, prepared and served. In hospitals and other places, tiles and walls must also be kept as germ-free as practicable.

In the past, germicides and disinfectants have been provided to clean apparatus and containers used for the preparation and packaging of foods and beverages and for the cleaning of articles such as plates, cups, glasses, etc., all of which may be subject to microbial contamination. It has also been known that certain amines may be reacted with a silicone compound to provide a silanized amine for inhibiting the growth of bacteria and fungi, as set forth in U.S. Pat. No. 3,719,697 and in the controlling of algae, as set forth in U.S. Pat. No. 3,730,701.

We have now found that antimicrobial compounds and particularly phenolic compounds can be silanized to provide new and useful silanized antimicrobial compounds which can be adhered to a variety of things such as bottles, filter media, crockery, floors, polymeric substances, and the like through the silane moiety. The silanized antimicrobial compounds of this invention are preferably prepared by the method disclosed in our co-pending application Ser. No. 501,022 filed Mar. 3, 1974, now abandoned, entitled "Method of Synthesizing Silanized Antimicrobial Compounds and Method of Use" which is hereby incorporated by reference.

Accordingly, it is an object of this invention to provide silanized antimicrobial compounds.

Other objects of the invention will in part be obvious and will in part appear hereinafter.

The invention accordingly comprises the silanized antimicrobial compounds which are exemplified herein and the scope of the invention will be indicated in the claims.

SUMMARY OF THE INVENTION

The silanized antimicrobial compounds of the invention are the reaction products of a compound having the formula $NH_2(CH_2)_nSi(R)_3$ wherein R is methoxy, ethoxy or propoxy and $n$ is 2, 3, or 4 and which is combined with a reactant compound which is a chlorinated phenol, bis-phenol, dihydric phenol or hydroxy diphenyl ether, or ortho or para hydroxybenzoic acid or the 1 to 12 carbon alkyl esters thereof.

The general formula for the silanized compound is believed to be

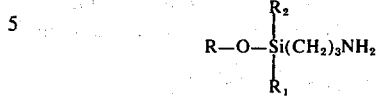

wherein R is the antimicrobial reactant radical, and $R_1$ and $R_2$ are methoxy, ethoxy or propoxy, and n is 2, 3, or 4.

Of the class of silanized antimicrobial compounds in accordance with the invention, the most preferred compounds are the reaction product of hexachlorophene, pentachlorophenol and 2, 4, 4'-trichloro-2' hydroxyphenyl ether, all silanized with γ amino triethoxy silane.

It is believed that the silanized hexachlorophene has the formula

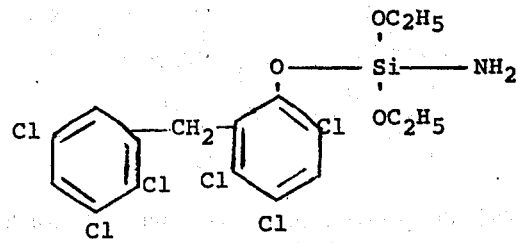

It is believed that the silanized pentachlorophenol has the formula

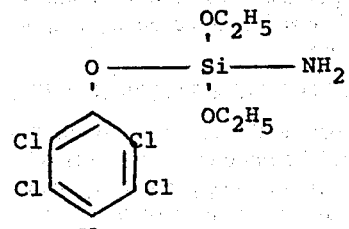

It is believed that the silanized 2, 4, 4'-trichloro-2' hydroxyphenyl ether has the formula

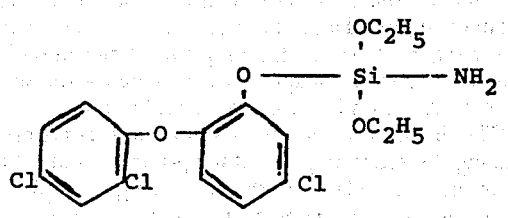

The preferred silanizing agent is γ amino propyl triethoxy silane which is reacted in an organic solvent for both the silane and the antimicrobial compound, preferably chloroform. The reactants are heated until the reaction is substantially complete and the resulting silanized antimicrobial compound is isolated by washings with e.g. petroleum ether and/or water.

Besides the preferred hexachlorophene, pentachlorophenol and 2, 4, 4'-trichloro-2' hydroxyphenyl ether, the other antimicrobial reactants which may be silanized to form compounds in accordance with the invention are dichlorophene, o-benzyl p-chlorophenol, pentachlorophenol, ortho or para hydroxybenzoates having from 1 to 12 carbon atoms in the alkyl chain (of these, heptyl and octyl are preferred), salicylic acid and hexyl resorcinol.

The reaction in silanizing hexachlorophene which is illustrative of the method for synthesizing the silanized antimicrobial compound of the invention is as follows:

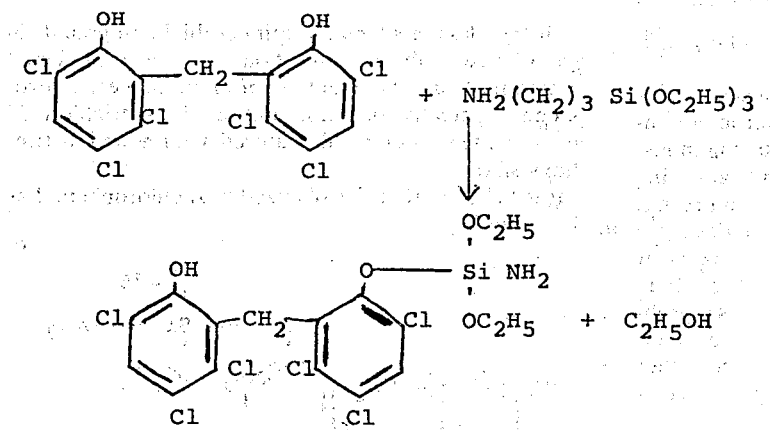

Thus the phenolic compound, such as hexachlorophene, is joined to the silicon atom through the oxygen of a hydroxyl group to produce the silanized antimicrobial compound with ethyl alcohol as the reaction product. The silanized antimicrobial compounds of the invention may be either solid or in liquid form. The silanized compounds have melting points generally lower than unsilanized antimicrobial compounds by about 50°C. or more.

DETAILED DESCRIPTION OF THE INVENTION

As set forth in the examples hereinafter, a number of antimicrobial compounds have been silanized by reaction with γ amino propyl triethoxy silane to form silanized derivatives which substantially retain the antimicrobial properties of the original antimicrobial compound while at the same time being capable of being bound to glass, to siliceous or other surfaces.

An examplary and a preferred reaction of hexachlorophene with the γ amino propyl triethoxy silane results in a silanized hexachlorophene derivative which is formed by the splitting out of ethyl alcohol from the silane compound and the attachment of silicon through the oxygen of one hydroxyl group of the hexachlorophene. The reaction appears to be true for the silanization of the antimicrobials set forth herein.

The hypothesis of the reaction was confirmed by testing the reaction product for primary amine (fluorescamine method) with the test being positive. Mass spectroscopy and nuclear magnetic resonance spectroscopy studies were also performed and these tests indicate that the silanized hexachlorophene is joined through the oxygen of one hydroxyl group to the silicon of the silanizing amine as shown in the above formula for silanized hexachlorophene. Infrared spectra and analysis for silicon show the presence of silicon in the reaction product to an extent consistent with the above formula.

The silanized hexachlorophene has a molecular weight of 579 and exhibits excellent microbiocidal properties. The silane moiety of the compound provides strong bonding for the monomolecular coating of surfaces.

The same reaction as set forth above for the silanization of hexachlorophene has also been used to produce silanized dichlorophene, o-benzyl p-chlorophenol, pentachlorophenol, heptyl p-hydroxybenzoate, octyl p-hydroxybenzoate, salicylic acid, 2, 4, 4'-trichloro-2'-hydroxyphenyl ether, and hexyl resorcinol.

The above compounds had been silanized by γ amino propyl triethoxy silane and it has been concluded that the reaction set forth for hexachlorophene above is general for such compounds. The compounds all retain excellent antimicrobial properties and bonding properties to a number of substrates.

The silane moiety is joined through the oxygen of an hydroxyl group of the antimicrobial starting compound. The retention of substantial antimicrobial action of the silanized compounds of the invention is unexpected, since the hydroxyl group of phenolic and other such antimicrobial compounds has been considered as essential for antimicrobial activity. In the case of those silanized derivatives where the starting antimicrobial compound has only one hydroxyl group it is even more unexpected, since the hydrogen of the hydroxyl group is replaced by the silane moiety.

The general reaction comprises the admixing of the antimicrobial compound with γ amino propyl triethoxy silane in a solvent for both compounds, preferably chloroform. Triethylamine was originally thought to provide a catalytic function in the reaction but later work indicates that the triethylamine probably is not required. The mixture is refluxed for about 75 to 90 minutes and near the end of the refluxing about 50% or more of the chloroform is boiled off. The solution (or suspension) is then permitted to cool to room temperature and about 4 to 5 volumes of petroleum ether (b.p. 40°–60°C.) are added to it with good mixing. At this point the compounds with high melting points (120°C. and above) are generally precipitated (often as amorphous masses) after the silanization with the addition of petroleum ether. After standing overnight at room temperature the silanized derivatives of higher melting points become crystalline.

The mother liquor is then poured off and the crystals are washed several times with about four volumes of petroleum ether. Finally the crystals are suspended in 2 volumes of petroleum ether and well ground with a mortar and pestle to wash out impurities. The crystals are then removed from the mother liquor by centrifugation or filtration and again washed several times with about 4 volumes of petroleum ether, filtered and are air-dried. The silanized antimicrobial composition obtained by this method is pure, having a sharp melting point and a good infrared spectrum. Usually the silanized compositions have melting points that are substantially lower than that of the original composition by 50°C. or more. With those antimicrobial reactant compositions having lower melting points (100°C. or lower) it was found that precipitation with petroleum ether did not yield crystalline material, but usually gummy masses. Dichlorophene, when silanized with the above method, yielded a derivative having a melting point of 48°C. and the compound invariably became gummy upon standing. Dichlorophene itself has a melting point of 163°C.

It was found that these gummy precipitates were insoluble in water but could be extensively washed with water to remove impurities such as the excess silane coupling agent and triethylamine. The washed residue is soluble in methanol and analysis of the methanolic solutions readily indicated the presence of the silanized compound. The following examples are illustrative of the methods of the invention and should not be considered limiting.

EXAMPLE I

Silanized Hexachlorophene 10 g. of hexachlorophene is placed in a 100 ml. two necked round bottom flask. To the flask is added 75 ml. of chloroform, 3.3 ml. of triethylamine, and 7 ml. of $\gamma$ amino propyl triethoxy silane. A few boiling chips are also added. The mixture is refluxed (63° – 69°C.) for 75 minutes. After cooling, the contents of the flask are removed to a 500 ml. stoppered glass container and 300 ml. of petroleum ether (b.p. 40° – 60°C.) are added, and let stand in the refrigerator overnight for crystallization. On the following day the supernatant liquid is poured off and the crystals again suspended in 200 ml. of petroleum ether, mixed well, permitted to settle and the supernatant poured off. Then the crystals are suspended in about 50 ml. of petroleum ether, ground well in a mortar and pestle, 150 ml. of petroleum ether added and again let settle. The clear supernatant liquid is poured off. Washing with 150 ml. of petroleum ether is repeated three more times. After the final wash the crystals are filtered on filter paper and permitted to air dry. The yield is 14.0 g. (96.6% of theory), m.p. 110°–111°C. Crystals are cream colored. Infrared spectrum shows presence of silicon-containing group. Analysis for primary amine is positive.

EXAMPLE II

Silanized Dichlorophene 2 g. of dichlorophene is added to 25 ml. of chloroform in a 2 necked pear-shaped flask. To the mixture are added 2 ml. of $\gamma$-NH$_2$(CH$_2$)$_3$Si(OC$_2$H$_5$)$_3$ and 1 ml. of triethylamine and a few boiling chips. The mixture goes completely into solution and is refluxed for 60 minutes. After refluxing, about 50% of the chloroform is evaporated off. Then the solution is cooled and 75 ml. of petroleum ether added to give a gummy precipitate after standing in the refrigerator overnight. The supernatant liquid is poured off and 20 ml. of fresh petroleum ether added with good mixing. A solid precipitate forms. Precipitate is permitted to settle and the clear supernatant poured off. Twenty ml. of fresh petroleum ether is added and again after settling of precipitate the supernatant liquid is removed. This operation is repeated three more times until the precipitate changes from a gummy to a hardened, friable mass. The latter is ground to a powder, filtered and air dried. Yield is 1.7 g. (about 50% of theory) of a cream white powder with a melting point of 48°C. The I.R. spectrum shows the presence of a silicon-containing group. The powder tends to become gummy on standing overnight in a capped vial in a desiccator. This was observed on three separate preparations.

EXAMPLE III

Silanized Heptyl-p-hydroxy benzoate 2 gm. of heptyl-p-hydroxy benzoate are added to 25 ml. of chloroform in a 2 necked pear-shaped flask. Then there is added 1 ml. of triethylamine and 2 ml. of $\gamma$ amino propyl triethoxy silane and the contents of the flask are mixed until the heptyl p-hydroxybenzoate is dissolved. A few more boiling chips are added and the mixture is refluxed for one hour, boiling off most of chloroform. An insoluble residue is obtained. (Note: This residue yields a gummy mass which resists all efforts at crystallization when treated with petroleum ether as prescribed for dichlorophene synthesis). Then add 30 ml. of water to residue and mix well with a stirring rod for several minutes. Let settle and separate aqueous layer. Repeat washing with 30 ml. of water four more times to completely removed any unreacted triethylamine, $\gamma$ amino propyl triethoxy silane and other impurities. A cleaned residue of about 2 – 3 grams of silanized heptyl p-hydroxybenzoate is obtained. It is completely dissolved in 10 ml. of methanol to yield a 15 to 20 % solution, which can be suitably diluted with methanol for use or testing purposes. Tests indicate the material in solution is hydrophobic and gives a positive reaction for primary amines. These tests indicate reaction between the heptyl p-hydroxybenzoate and the silane coupling reagent. The procedure given in this synthesis is an alternate for that used to silanize hexachlorophene and is applicable to silanized phenols which cannot be crystallized by treatment with petroleum ether.

EXAMPLE IV

Silanized o-benzyl-p-chlorophenol (BCP)

2 gm. of o-benzyl-p-chlorophenol are added to 25 ml. of chloroform in a 2 necked pear-shaped flask. Then 1 ml. of triethylamine and 2 ml. of $\gamma$ amino propyl triethoxy silane are added and mixed until the BCP completely dissolves and the flask contents are then refluxed for one hour. After refluxing, most of chloroform is boiled off. A grey-brown viscous liquid residue is obtained of 2 – 3 ml. in volume. It is washed by mixing with a glass rod with 30 ml. of water for several minutes. After settling, the aqueous top layer is poured off, and washing with 30 ml. of water is repeated three more times. The insoluble residue is dissolved in 10 ml. of alcohol to yield a pale yellow 15 – 20% solution of silanized o-benzyl-p-chlorophenol. Tests on this solution show the contents are hydrophobic whereas the original o-benzyl-p-chlorophenol is not. Also a positive indication for primary amines is obtained. Both tests are evidence of the silanization of BCP.

EXAMPLE V

Silanized Pentachlorophenol (PCP)

2 grams of pentachlorophenol is added to 25 ml. of chloroform in a 2 necked pear-shaped flask. To the contents are then added 1 ml. of triethylamine and 2 ml. of γ amino propyl triethoxy silane and mixed until the PCP is dissolved. Then the solution is refluxed for one hour and most of the chloroform is boiled off. Then three volumes of petroleum ether (b.p. 40°–60°C.) are added to the residue, mixed well with a stirring rod, and let stand overnight at room temperature. A white crystalline precipitate forms. The supernatant liquid is poured off and the precipitate washed with 30 ml. of petroleum ether and after settling, the supernatant liquid is poured off. The precipitate is washed three more times with 30 ml. of petroleum ether each time. Then after removing the final supernatant liquid, the precipitate was air dried. A creamy white powder weighing 3.2 g. and having a melting point of 121°C. was obtained. Analysis of the powder showed the presence of Si by I.R. spectrum, a primary amine, and hydrophobicity to confirm silanization of pentachlorophenol.

EXAMPLE VI

Silanized 2, 4, 4'-Trichloro-2'-Hydroxydiphenyl Ether (THDP)

Two and one-half grams of THDP (sold by Ciba-Geigy as Irgasan DP 300) are added to 25 ml. of chloroform. Then 1 ml. of triethylamine and 2 ml of γ amino propyl triethoxy silane are added to the chloroform solution and the mixture (a clear solution) refluxed for 1 hour. After refluxing, most of the chloroform is boiled off, leaving 3 ml. of a clear yellow viscous liquid. This liquid is then washed with 40 ml. of water using a stirring rod. After separation of layers, the supernatant is separated and the residue is washed with 40 ml. of water. This is repeated 4 more times to completely remove impurities and residual triethyl amine and γ amino propyl triethoxy silane. The residue is dissolved in 10 ml. of methanol to give a 15 – 20% solution of silanized THDP. Tests of this solution confirm the formation of the silanized derivative. It was observed that on standing overnight in the refrigerator, two layers formed in the methanol solution. The high concentration of the silanized THDP appeared to cause this, since a more dilute solution remains unchanged.

EXAMPLE VII

Silanized Salicyclic Acid

Two grams of salicylic acid are mixed into and dissolved in 25 ml. of chloroform. To the solution is added 1 ml. of triethylamine and 2 ml. of γ amino propyl triethoxysilane and the solution is refluxed for 75 minutes. Near the end of refluxing most of the chloroform is boiled off. The residue is washed 8 times with 40 ml. of petroleum ether (b.p. 40° to 55°C.) in order to remove unreacted material. The residue is then dissolved in 25 ml. of methanol to yield a yellow solution. This solution when reacted with glass shows positive hydrophobicity test and a positive test for primary amines. These tests are indicative of silanization of salicylic acid.

EXAMPLE VIII

Silanized Octyl p-Hydroxybenzoate

Two grams of octyl p-hydroxybenzoate is added to 25 ml. of chloroform and mixed well. To the solution is added 1 ml. of triethyl amine and 2 ml. of γ amino propyl triethoxy silane and the solution is refluxed for 60 minutes. Near the end of refluxing most of the chloroform is boiled off. The residue is washed thoroughly with good mixing 5 times with 40 ml. of water each time. Then the residue is dissolved in 10 ml. of methanol yielding a 14 ml. solution containing about 2.5 g. of silanized octyl p-hydroxybenzoate. Tests with this solution after reacting it with glass gave a positive hydrophobicity reaction and the solution also gave a strongly positive primary amine reaction. Both of these tests indicate silanization of octyl-p-hydroxybenzoate.

EXAMPLE IX

Silanized Hexyl Resorcinol

Two grams of hexyl resorcinol is added to 25 ml. of chloroform and mixed well. To the solution is added 1 ml. of triethyl amine and 2 ml. of γ amino propyl triethoxy silane and the solution is refluxed for 60 minutes. Near the end of refluxing most of the chloroform is boiled off. The residue is washed thoroughly 5 times with 40 ml. of water each time. After the final wash the red, wine-colored residue is dissolved in 10 ml. of methanol to yield 15 ml. of solution containing about 2.5 g. of silanized hexyl resorcinol. Tests with this material on glass indicated a high degree of hydrophobicity. Also, the solution gave a high positive test for primary amines. Both these tests indicate formation of silanized hexyl resorcinol.

The formulas for the above antimicrobial compounds silanized by γ amino propyl triethoxy silane are believed to be:

1. Silanized Hexachlorophene

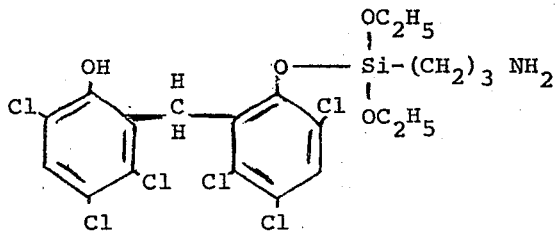

2. Silanized 2, 4, 4'-trichloro-2' hydroxyphenyl ether (THDP)

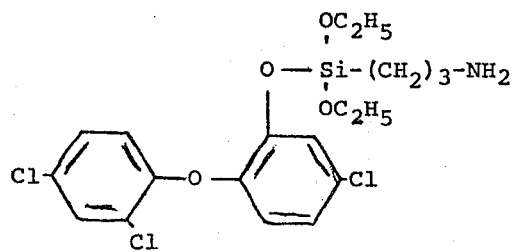

3. Silanized Dicholorophene

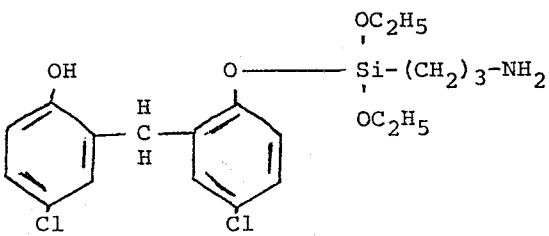

4. Silanized Pentachlorophenol

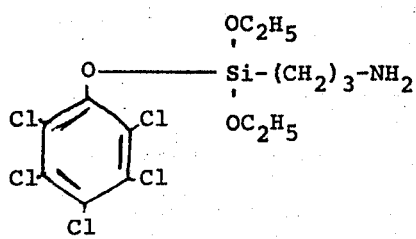

5. Silanized p-Hydroxybenzoic Acid

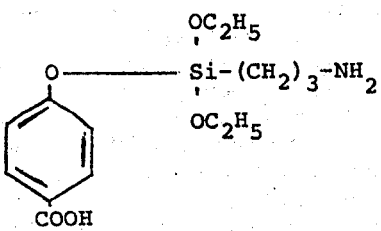

6. Silanized Ethyl p-Hydroxybenzoate

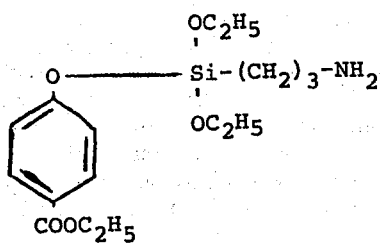

7. Silanized Heptyl p-Hydroxybenzoate

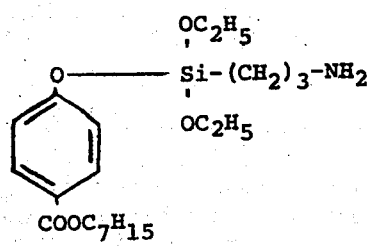

8. Silanized Octyl-p-Hydroxybenzoate

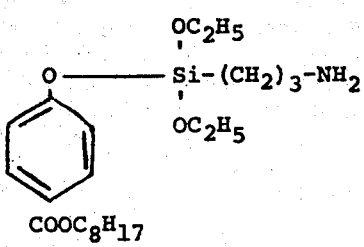

9. Silanized-O-Benzyl-p-Chlorophenol

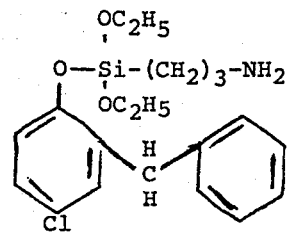

10. Silanized Hexylresorcinol

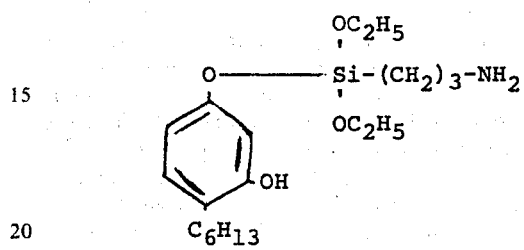

11. Silanized Salicylic Acid - O-Hydroxybenzoic Acid

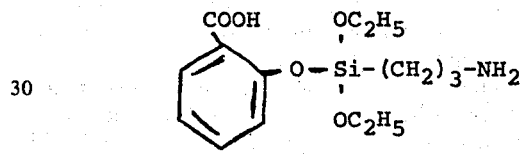

The melting points of the original antimicrobial compounds are compared with the melting points of the silanized derivatives in Table A.

TABLE A

|  | m.p. °C. Original Antimicrobial | m.p. °C. Silanized Antimicrobial |
| --- | --- | --- |
| Hexachlorophene | 161–162 | 111–113 110–111 114 |
| Dichlorophene | 163 | 48 |
| 2, 4, 4'-trichloro-2' hydroxydiphenyl ether | 57 | Liquid at 40°C. |
| Pentachlorophenol | 189 | 121 122–124 |
| p-Hydroxybenzoic Acid | 213 | Liquid at 40°C. |
| Ethyl-p-Hydroxybenzoate | 117 | Liquid at 40°C. |
| Heptyl-p-Hydroxybenzoate | 47–48 | Liquid at 40°C. |
| O-Benxyl-p-Chlorophenol | 45 | Liquid at 40°C. |
| Octyl-p-Hydroxybenzoate |  | Liquid at 40°C. |
| Hexylresorcinol | 68 | Liquid at 40°C. |
| Salicylic Acid (O-Hydroxybenzoic Acid) | 158 | Liquid at 40°C. |

The adherence of silanized hexachlorophene made in accordance with Example I above was tested by applying the silanized hexachlorophene onto filer media, onto small glass beads and onto a glass slide. The silanized hexachlorophene was quantitatively determined before being applied to the filter media, a hydrothermally formed magnesium silicate (sold by the assignee herein under the trademark Clearfil) and was then subjected to a buffer wash of ammonium bicarbonate having a ph of 7.0 and the amount of silanized hexachlorophene removed was measured. This wash was then followed by a 0.1 N alkaline-methanol wash and a final wash with 1.0 N NaOH at 70°C. In each instance the amount of silanized hexachlorophene in the filtrate was measured. The same procedure was used for the coating of small glass beads and the glass slides. Approximately 50% of the original silanized hexachlorophene bonded on the siliceous materials remained even after extensive chemical washing with hot alkali.

The silicon bonding of the silanized antimicrobials of the invention provides for a number of antimicrobial uses where bonding of the antimicrobial to a siliceous surface is important. Examples of some of these uses include the coating of a variety of containers for beverages, foods, medicinals, and the like, such as glass bottles, cans or packages having an inner surface or liner to which the silane moiety of the silanized antimicrobial will adhere. Further, the silanized antimicrobials may be applied to floors and walls of tile or other materials in hospitals, schools, bathrooms, kitchens, and the like. The silanized antimicrobials may also be coated on filter media such as sand, diatomaceous earth, asbestos or other siliceous materials, on glass beads or on chemical apparatus such as reaching rings for liquid treatment. Besides the adherence of the silanized antimicrobials to siliceous surfaces, it may also be possible to apply the silanized antimicrobial compounds into or onto fabrics, cellulosic filters, leather, or onto metals or other such surfaces. The silanized antimicrobial compounds of the invention can be applied to dishes and glassware from a water medium, e.g. when dishes are washed in a hospital or resturant the silanized antimicrobial compound may be applied as part of the washing operation.

To test the antimicrobial action of the above silanized compounds the following procedure was used. A freshly prepared microbial culture was diluted to about $10^4 - 10^5$ cells per ml. To each dilution, 6 drops of a wetting agent (Makon 10) were added and five-tenths of a ml aliquot portions of the dilution were then pipetted onto a number of petri dishes. The petri dishes had been treated with silanized antimicrobial compounds as shown in Table I below with the controls being cleaned and untreated. The petri dishes with the pipetted cultures on them were swirled so that the microbial suspension was evenly distributed and then were allowed to stand for about 30 minutes. Thereafter, 10 ml of phosphate buffer solution was added to the control petri dishes. The dishes were again swirled and the dishes were then pour plated with MYGP for yeast and PCA for bacteria. MYGPA is an agar mixture with each liter containing 3 grams of yeast extract, 3 grams of malt extract, 5 grams of peptone, 10 grams of dextrose, and 10 grams of agar. PCA is a plate count agar. The petri dishes treated with silanized antimicrobial coatings were directly pour plated with media using MYGP for yeast and PCA for bacteria. Duplicate plate counts were made for each microorganism. The results are set forth in Table I with the number of microorganisms counted for the control petri dishes and those treated with silanized antimicrobial compounds shown as the number of microorganisms per milliliter.

TABLE I

| Microorganism | Controls | Silanized Dichlorophene | Silanized Pentachlorophenol | Silanized Hexachlorophene | Silanized Benzylchlorophenol | Silanized N-Heptyl-P-Hydroxybenzoate |
|---|---|---|---|---|---|---|
| E. coli | $1.4 \times 10^4/1.7 \times 10^4$ | 0/0 | 14/19 | 138/188 | 136/142 | 5/6 |
| B. subtilis | $8.4 \times 10^5/9.1 \times 10^5$ | 135/73 | 551/501 | 206/813 | 68/249 | 218/195 |
| S. diastaticus | $2.7 \times 10^3/2.3 \times 10^3$ | 13/26 | 5/20 | 37/21 | 10/15 | 10/9 |

The results of Table I show substantial antimicrobial action still retained by the silanized antimicrobial with excellent bonding properties to the petri dish. As would be expected, the antimicrobial activity of each silanized compound may vary with the microorganism and from plate to plate. In other tests the count even for one plate was at substantial variance with the other plate, due to experimental errors or difficulties in recovering the organisms from the treated surfaces, or variations in drying or timing.

To test the persistance of the antimicrobial action after washing, petri dishes were treated with silanized hexachlorophene and 2, 4, 4'-trichloro-2' hydroxyphenyl ether (THDP). The petri dishes were dried at 40°C. overnight and then washed in a 4% solution of sodium hydroxide at 70°C. for 20 minutes and then rinsed with tap water. The sodium hydroxide washing and water rinsing cycle was then repeated 5 times and the treated and washed petri dishes were dried at 40°C. for one hour before testing. Cultures as prepared above were then inoculated onto the petri dishes and the number of microorganisms on duplicate plates were enumerated after standing for approximately 30 minutes.

The results of these tests are set forth in Table II.

TABLE II

| | E. coli | B. subtilis | S. diastaticus |
|---|---|---|---|
| Control | 830,000/1,210,000 | 35,000/33,000 | 800/500 |
| Silanized THDP | 5/49 | 105/82 | 10/33 |
| Silanized Hexachlorophene | 720/210 | 340/670 | 170/40 |

From the results shown in Table II it is apparent that the silanized compounds had strong antimicrobial properties even after repeated hot alkali washing. This indicates that coatings of silanized antimicrobials of the invention when applied to dishes, glassware, walls, and the like can withstand hot washings and still retain their antimicrobial properties. It also demonstrates that the tenaciousness of the silane bonding would make it necessary to apply a thin film of silanized antimicrobial compound to tiles, dishes, or the like only periodically and that when used as a lining for bottles no appreciable amount could be easily removed from the bottle surface.

A preferred commercial composition is a mixture of silanized hexachlorophene and THDP. To test the efficacy of the silanized mixture, the following tests were performed. Mixed silanized hexachlorophene and THDP were applied from dilute methanol and water solutions onto petri dishes with a wetting agent in the amount of 0.5 ml on each plate. The control petri dishes were treated as in the tests set forth in Table I above. All petri dishes were then inoculated, allowed to stand for 30 minutes and were then plated in duplicate. The results are shown in Table III below.

TABLE III

| Control | Culture | Silanized hexachlorophene plus Silanized THDP | |
|---|---|---|---|
| | | 1 ml | 0.1 ml |
| $29\times10^6$ | E.coli | 0/0 | 0/0 |
| $36\times10^6$ | | | |
| $3\times10^3$ | B.subtilis | 0/0 | 0/0 |
| $3\times10^3$ | | | |
| $6\times10^3$ | S.diastaticus | 0/0 | 0/0 |
| $11\times10^3$ | | | |

As shown in Table III above, the controls showed a very substantial number of microorganisms while the combination of silanized hexachlorophene and silanized THDP showed no microorganisms for the duplicate plates from 1 ml or 0.1 ml aliquots of the recovery buffer.

To further test the efficacy of mixed silanized hexachlorophene and THDP as a commercial product for the antimicrobial treatment of surfaces, petri dishes were again treated with a mixture as for Table III above and dried at 40°C. for 24 hours. The petri dishes were then washed with methanol and water, which would remove any unbonded antimicrobial material. The microorganisms, in suspension, and wetting agent were applied in the amount of 0.5 ml on each plate which were then read in duplicate for the controls and treated plates. The results are set forth in Table IV below.

TABLE IV

| Culture | Control | Silanized THDP and Hexachlorophene | |
|---|---|---|---|
| | | 1 ml | 0.1 ml |
| E.coli | $8/11\times10^6$ | 0/0 | 0/0 |
| B.subtilis | $32/26\times10^3$ | 0/0 | 0/0 |
| S.diastaticus | $2/1\times10^2$ | 0/0 | 0/0 |

Again the combination of silanized hexachlorophene and silanized THDP effectively eliminated the microorganisms on the test plates and it is demonstrated that the silanized derivatives are bonded to the glass substrates.

EXAMPLE X

Hexachlorophene was also silanized with γ (beta-aminoethyl) amino propyl trimethoxy silane as follows. 3.5 grams of hexachlorophene were combined with 2 ml of γ (beta-aminoethyl) amino propyl trimethoxysilane in 25 ml of chloroform. The mixture was refluxed for about 1 hour to boil off most of the chloroform. Fifty ml of petroleum ether was then added and the resulting gummy mass was washed as in the above examples. It is believed that the hexachlorophene is joined to the silane moiety through the oxygen of one of the hydroxyl groups, replacing a methoxy group on the silicon atom.

The antimicrobial compounds of the invention may be used alone or in combination to provide a broad spectrum of antimicrobial action. The efficacy against bacteria, fungi, yeast, and the like varies from compound to compound and thus the antimicrobial silanized compounds may be used alone for a specific antimicrobial function or in combinations of two or more compounds for antimicrobial action against a number of microorganisms.

It should be further understood that the above examples and tests are for illustrative purposes and should not be considered as limiting.

What is claimed is:

1. An antimicrobial silanized compound having the formula

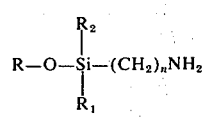

wherein R is a radical taken from the group consisting of a chlorinated phenol, bis-phenol or diphenyl ether, a 6 to 9 carbon atom alkyl or chlorine substituted dihydric phenol, an ortho or para hydroxybenzoic acid or a 1 to 12 carbon atom alkyl ester thereof; $R_1$ and $R_2$ are methoxy, ethoxy or propoxy; and $n$ is 2 to 4.

2. An antimicrobial silanized compound having the formula

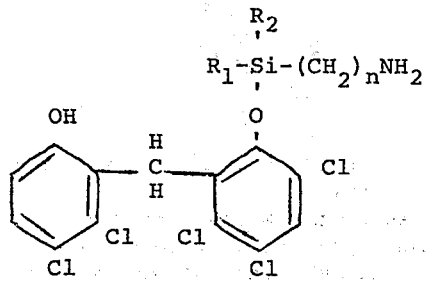

wherein $R_1$ and $R_2$ are methoxy, ethoxy or propoxy, and $n$ is 2 to 4.

3. An antimicrobial silanized compound having the formula

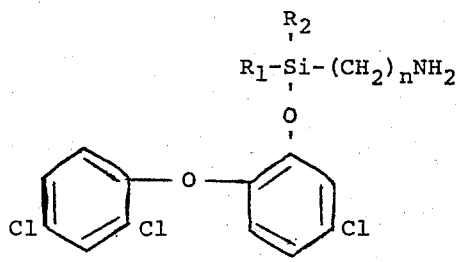

wherein $R_1$ and $R_2$ are methoxy, ethoxy or propoxy and $n$ is 2 to 4.

4. An antimicrobial silanized compound being the reaction product of

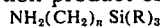
$NH_2(CH_2)_n Si(R)_3$ wherein R is methoxy, ethoxy or propoxy and $n$ is 2 to 4, combined with a reacting compound taken from the group consisting of chlorinated phenols, bis-phenols and diphenyl ethers; 6 to 9 carbon atom alkyl or chlorine-substituted dihydric phenols; ortho or para hydroxybenzoic acids or 1 to 12 carbon atom alkyl esters thereof.

5. The antimicrobial silanized compound of claim 4 wherein said reacting compound is hexachlorophene.

6. The antimicrobial silanized compound of claim 4 wherein said reacting compound is dichlorophene.

7. The antimicrobial silanized compound of claim 4 wherein said reacting compound is o-benzyl p-chlorophenol.

8. The antimicrobial silanized compound of claim 4 wherein said reacting compound is pentachlorophenol.

9. The antimicrobial silanized compound of claim 4 wherein said reacting compound is taken from the group consisting of heptyl p-hydroxybenzoate and octyl p-hydroxybenzoate.

10. The antimicrobial silanized compound of claim 4 wherein said reacting compound is salicylic acid.

11. The antimicrobial silanized compound of claim 4 wherein said reacting compound is 2, 4, 4'-trichloro-2' hydroxyphenyl ether.

12. The antimicrobial silanized compound of claim 4 wherein said reacting compound is hexyl resorcinol.

13. An antimicrobial compound having the formula

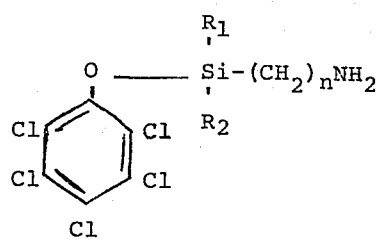

wherein $R_1$ and $R_2$ are methoxy, ethoxy or propoxy and $n$ is 2, 3, or 4.

14. An antimicrobial compound which is the reaction product of γ amino propyl triethoxy silane and a reactant compound taken from the group consisting of chlorinated phenols, bis-phenols and hydroxy diphenyl ethers; 6 to 9 carbon atom alkyl or chlorine substituted dihydric phenols; ortho or para hydroxybenzoic acids or the 1 to 12 carbon atom alkyl esters thereof.

15. The antimicrobial compound of claim 14 wherein the formula is

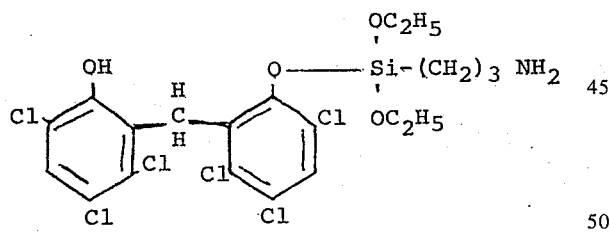

16. The antimicrobial compound of claim 14 wherein the formula is

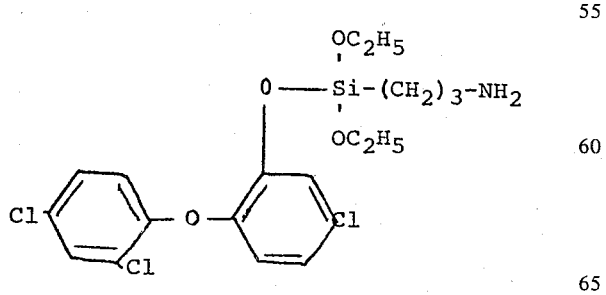

17. The antimicrobial compound of claim 14 wherein the formula is

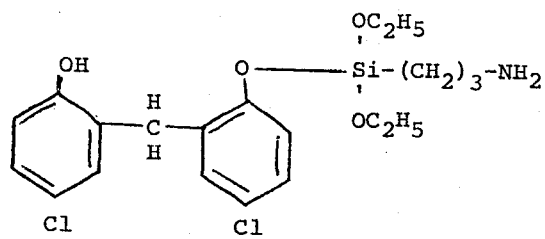

18. The antimicrobial compound of claim 14 wherein the formula is

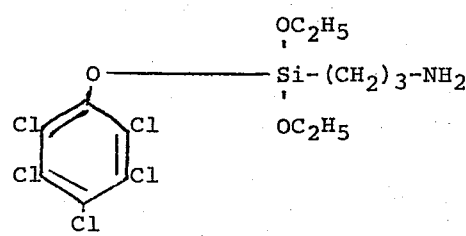

19. The antimicrobial compound of claim 14 wherein the formula is

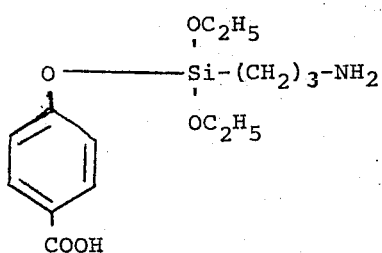

20. The antimicrobial compound of claim 14 wherein the formula is

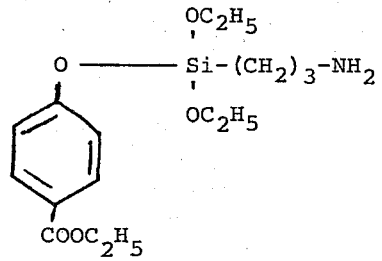

21. The antimicrobial compound of claim 14 wherein the formula is

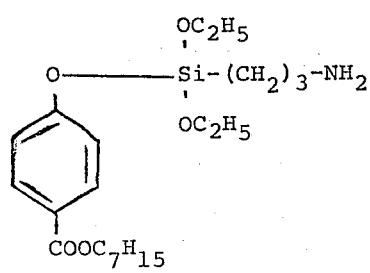

22. The antimicrobial compound of claim 14 wherein the formula is

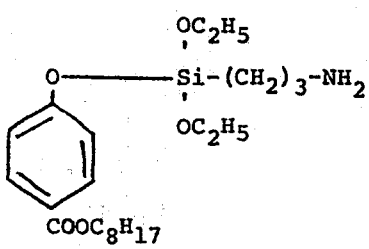

23. The antimicrobial compound of claim 14 wherein the formula is

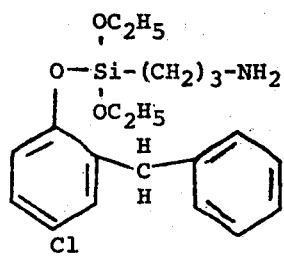

24. The antimicrobial compound of claim 14 wherein the formula is

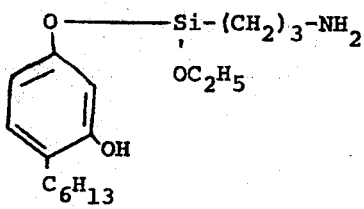

25. The antimicrobial compound of claim 14 wherein the formula is

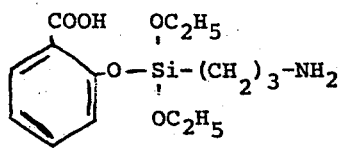

26. An antimicrobial compound which is the product of X—NH(CH$_2$)$_n$ Si(R)$_3$ wherein X is hydrogen or an amino lower alkyl having from 1 to 4 carbon atoms, R is methoxy, ethoxy or propoxy and $n$ is 2, 3, or 4; reacted with an antimicrobial starting compound taken from the group consisting of a chlorinated phenol, bis-phenol or hydroxy diphenyl ether, a 6 to 9 carbon atom alkyl or chlorine substituted dihydric phenol, an ortho or para hydroxybenzoic acid or a 1 to 12 carbon atom alkyl ester thereof.

* * * * *

UNITED STATES PATENT OFFICE
CERTIFICATE OF CORRECTION

PATENT NO. : 3,940,430
DATED : February 24, 1976
INVENTOR(S) : Mortimer W. Brenner and Louis Laufer It is certified that error appears in the above-identified patent and that said Letters Patent are hereby corrected as shown below:

ABSTRACT, line 7, "$NH_2(CH_2)_3 Si(R)_3$" should be --$NH_2(CH_2)_n Si(R)_3$--.
Column 1, line 12, "$NH_2(CH_3 Si(R)_3$" should be --$NH_2(CH_2)_n Si(R)_3$--.
Column 2, line 5, "$R-O-Si(CH_2)_3NH_2$" should be --$R-O-Si(CH_2)_nNH_2$--;
line 17, between "amino" and "trie-" insert --propyl--.
Column 3, line 47, "examplary" should be --exemplary--.
Column 6, line 27, "removed" should be --remove--.
Column 7, line 45, "Salicyclic" should be --Salicylic--.
Column 10, line 59, "filer" should be --filter--.
Column 11, line 32, "reaching" should be --raschig--;
line 59, "MYGPA" should be --MYGP--.
Column 14, line 30, Add a --Cl-- at the No. 6 position of the left benzine ring.

Signed and Sealed this eighteenth Day of May 1976

[SEAL]

Attest:

RUTH C. MASON
Attesting Officer

C. MARSHALL DANN
Commissioner of Patents and Trademarks